United States

Weil

4,049,754

Sept. 20, 1977

[54] TRIBROMONEOPENTYL PHOSPHORUS REACTIVE FLAME RETARDANTS

[75] Inventor: Edward D. Weil, Hastings-on-Hudson, N.Y.

[73] Assignee: Stauffer Chemical Company, Westport, Conn.

[21] Appl. No.: 726,077

[22] Filed: Sept. 23, 1976

[51] Int. Cl.$^2$ ............................. C07F 9/09; C07F 9/11; C07F 9/14; C07F 9/40

[52] U.S. Cl. .................................. 260/952; 8/116 P; 106/15 FP; 260/45.7 P; 260/45.85 E; 260/45.9 NP; 260/45.95 R; 260/950; 260/953; 260/956; 260/959; 260/960; 260/961; 260/963; 428/277

[58] Field of Search .............. 260/952, 953, 956, 959, 260/960, 961, 963, 950

[56] References Cited

U.S. PATENT DOCUMENTS

| | | | |
|---|---|---|---|
| 3,324,205 | 6/1967 | Carpenter et al. | 260/963 |
| 3,830,886 | 8/1974 | Davis et al. | 260/953 |
| 3,859,394 | 1/1975 | Burke | 269/953 |

Primary Examiner—Richard L. Raymond

Attorney, Agent, or Firm—Richard P. Fennelly

[57] ABSTRACT

Compounds of the formula:

$$[(BrCH_2)_3CCH_2O]_2P(O)R$$

wherein R is a functional group selected from the group consisting of —CH=CH$_2$, —CH$_2$X, —OR'OC(O)CH=CH$_2$, —OR'OC(O)C(CH$_3$)=CH$_2$, —O(R'O)$_n$H, —OH, —Cl, and NR"R''', wherein R' is a C$_1$-C$_4$ alkylene group, wherein R" and R''' are the same or different and are selected from the group consisting of hydrogen, lower alkyl, e.g. C$_1$-C$_8$, preferably C$_1$-C$_4$, phenyl, hydroxyalkyl, e.g., hydroxy C$_1$-C$_8$, or, preferably hydroxy C$_1$-C$_4$, and allyl groups, wherein X is selected from the group consisting of chlorine and bromine and wherein n is an integer between 1 and 20 are disclosed. These compounds have flame retardancy characteristics and are useful either as flame retardant additives or as reactive flame retardants which can react to confer durable flame retardancy on textiles or other polymer products.

11 Claims, No Drawings

TRIBROMONEOPENTYL PHOSPHORUS REACTIVE FLAME RETARDANTS

TECHNICAL DESCRIPTION OF THE INVENTION

The present invention relates to tribromoneopentyl esters of phosphorus acids which exhibit reactive flame retardant properties. These compounds can be used as flame retardant additives, but have the particular feature of being flame retardant reactive components for textile finishing and, in some instances, as monomers which have flame retardant properties.

It is known that tribromoneopentyl alcohol can be made into certain phosphorus esters which have flame retardant additive characteristics. These esters can be used as flame retardant additives to confer flame retardancy on a variety of materials. Phosphates and alkyl- or arylphosphonates are, for example, described in U.S. Pat. No. 3,824,205 to Carpenter et al. Bis(tribromoneopentyl) tribromoneopentyl phosphonate is described in U.S. Pat. No. 3,456,041 to Burk et al. The compounds described in these two patents, however, differ significantly from the compounds of this invention since the former compounds lack structural members which will react with the textiles or polymers that one may desire to flame retard. The halogen atoms contained in those compounds of the prior art are all of the relatively unreactive neopentyl type, and their relative inertness limits their use to being merely additives rather than reactive flame retardant monomers.

The compounds of the present invention retain the advantage of these prior art compounds with respect to having their bromine content in the heat-stable and light stable tribromoneopentyl form. However, the compounds of the present invention, unlike the above-described prior art compounds, contain reactive structural units and therefore have a broader field of utility as reactive flame retardants. The compounds of this invention have the following structure:

where R can be $-CH=CH_2$, $-CH_2X$, $-OR'OC(O)CH=CH_2$, $-OROC(O)C(CH_3)=CH_2$, $-O(R-'O)_nH$, $-OH$, $-Cl$, and $-NR''R'''$, where R' is a lower alkylene or haloalkylene group, e.g., a $C_1-C_4$ group, R'' and R''' are the same or different and are selected from the group consisting of hydrogen, lower alkyl, e.g., $C_1-C_8$, preferably $C_1-C_4$, phenyl, hydroxy-lower-alkyl, e.g., hydroxy $C_1-C_8$ or, preferably $C_1-C_4$ alkyl and allyl groups, where X is a halogen, e.g., chlorine or bromine, and where n is an integer between 1 and 20. Preferred compounds are bis(tribromoneopentyl) vinylphosphonate, bis(tribromoneopentyl) chloromethylphosphonate, bis(tribromoneopentyl) acryloxyethyl phosphate, bis(tribromoneopentyl) acryloxypropyl phosphate, bis(tribromoneopentyl) methacryloxyethyl phosphate, bis(tribromoneopentyl) methacryloxypropyl phosphate, bis(tribromoneopentyl) acryloxychloropropyl phosphate, bis(tribromoneopentyl) methacryloxychloropropyl phosphate, bis(tribromoneopentyl) phosphorochloridate and bis(tribromoneopentyl) acid phosphate and its salts.

The compounds of this invention have reactive functional groups for R which are well adapted to serve as means for attaching the compounds to textiles. When R is vinyl or terminates in an acrylate or methacrylate group the compounds are polymerizable by free radical mechanisms and can be polymerized or copolymerized in situ on textiles by means of graft polymerization as described in U.S. Pat. No. 3,695,925 to Weil. These monomers can also be polymerized or copolymerized to form useful flame retardant emulsions, films, coatings and molding resins. When R is $CH_2X$, where X is a halogen, e.g., preferably chlorine or bromine, although permissably fluorine or iodine, the compound is sufficient reactive as an alkylating reagent to allow for attachment via an ether linkage to cellulose that has been treated with alkali in a manner similar to that described by Drake et al. in Textile Research Journal, Vol. 29: 270,884 (1959). When R is $-NR''R'''$ the compounds can phosphorylate cellulose in a manner described for phosphoramides by Morris et al. in Textile Research Journal, Vol. 43: 336 (1973), or when either R'' or R''', or both, are hydrogen or hydroxyalkyl, they can be bonded to textiles in the manner described in U.S. Pat. Nos. 2,838,228 to Glade et al., 3,767,736 to Burke, and 3,746,572 to Weil et al.

The vinyl and acrylic monomers of the invention can also be used to make flame retardent polymers and copolymers for films, sheets, molded objects, and coatings. The alcohol-group containing reactive compounds of the invention can furthermore be incorporated into flame retardant polyesters and polyurethanes by condensation polymerizations.

The phosphorochloridate, i.e., when R is $-Cl$, can be used per se as a reactive flame retardant in the phosphorylation process described by Kiselev and Danilov, Russian Pat. No. 159,524 or by Schwenker and Pascu, Textile Research Journal, Vol. 27, pp. 173 and following (1957), or can be converted to other useful products. It can, for example, be reacted with an epoxide, e.g., ethylene oxide, propylene oxide, epichlorohydrin, glycidyl acrylate, glycidyl methacrylate, optionally, in the presence of a suitable Lewis acid catalyst, such as $TiCl_4$, $AlCl_3$, etc., to obtain a phosphate having a primary chloroalkyl group. The phosphorochloridate group can alternatively be reacted with an amine, $HNR''R'''$, to obtain the phosphoramidates of the invention where R is $NR''R'''$. The phosphorochloridate can also be reacted with diols or polyols to make a hydroxyalkyl bis(tribromoneopentyl) phosphate which can be used as a reactive cellulose flame retardant by using the process described in U.S. Pat. No. 3,746,572 to Weil.

Compounds falling within the scope of the formula described above can be formed by reaction in the liquid phase, optionally in the presence of a non-polar organic solvent, e.g. benzene, toluene, xylene, a $C_5-C_{12}$ hydrocarbon, e.g., hexane, heptane, etc., of two molar equivalents of tribromoneopentyl alcohol with $Cl_2P(O)R$, where R is as defined above, by heating, e.g., between about 30° C – 100° C., until two molar equivalents of hydrochloric acid are given off, or, alternatively, with the addition of at least two moles of a suitable base, e.g., triethylamine, to abstract the two molar equivalents of hydrochloric acid. Heating can be used in the latter process embodiment to accelerate the process.

An alternative process for use in making bis(tribromoneopentyl) phosphorochloridate is the reaction of two molar equivalents of tribromoneopentyl alcohol with $POCl_3$, optionally in a non-polar organic solvent, with heating to drive off two molar equivalents of hydrochloric acid.

The compounds of the present invention have in general an advantage as flame retardant textile finishing compounds over related dibromopropyl esters known to the prior art. The present compounds show much greater resistance to heat, to light and to strong bases, e.g., harshly alkaline non-phosphate detergents. This latter advantage is of importance when the compounds are to be used in clothing, carpeting, draperies, furniture upholstery and the like. The vinyl containing monomeric compounds can also be copolymerized with other vinyl compounds, e.g., the vinyl halides, vinyl acetate and the vinylidene halides, into polymers which yield coatings, films, and molded articles possessing good light stability.

The following Examples illustrate the present invention:

EXAMPLE 1

A mixture of 129.5g tribromoneopentyl alcohol, 35g of vinylphosphonyl chloride, 78 ml. of triethylamine, and 300 ml. of methylene chloride was refluxed for one day then evaporated to dryness. The residue was redissolved in methylene chloride, was washed with water and sodium bicarbonate solution, and then was dried over magnesium sulfate, was filtered and was evaporated to 100° C. at 0.1 mm. The product was a viscous syrup which crystallized upon standing. The nuclear magnetic resonance (n.m.r.) spectrum showed a ratio of about 5.3 aliphatic protons/vinyl proton (theory — 16:3, or 5.33:1 for the indicated product).

After recrystallization from slightly aqueous ethanol, the product, bis(tribromoneopentyl) vinylphosphonate, was a crystalline solid having a melting point of 71°–72° C. Anal.: Calcd. for $C_{12}H_{19}O_3Br\ P$: %Br 66.5, %P 4.3; Found: %Br 67.0, %P 4.3.

EXAMPLE 2

A mixture of 33.5g vinyl chloride, 16.5g of the bis(tribromoneopentyl) vinylphosphonate, 15 ml of water, 15 ml of 1% polyvinyl alcohol solution, and 1.5 ml g 5% isopropyl peroxydicarbonate in heptane was charged to a polymerization vessel, and the mixture was agitated for 16 hours at 45° C. The suspension copolymer of vinyl chloride and bis(tribromoneopentyl) vinylphosphonate thus obtained was dried. A quantitative yield of polymer was obtained and an infrared spectrum on the material did not show any residual unsaturation from the phosphonate.

Comparison was made with representatives of prior art types of flame retarded acrylonitrile-butadiene-styrene (ABS) resins, those containing $Sb_2O_3$ and various chlorinated organic compounds and the ABS-polyvinyl chloride-$Sb_2O_3$ polyblends. The former tend to have reduced deformation temperatures under load. Several formulations containing the copolymer formed earlier in this Example were milled to obtain comparison data with flame retardant ABS. The results are summarized in the Table.

TABLE

| Sample No. | Blend Composition (*) | L.O.I.(***) | Physical Appearance |
|---|---|---|---|
| 1 | ABS** (Control) | 17.49 | Tough Sheet |
| 2 | ABS** + 22 phr. (parts per hundred) Dechlorane**** | 23.49 | Brittle |
| 3 | ABS** + 21 phr. copolymer from Example 2 and 2.3 phr. $Sb_2O_3$ | 21.39 | Tough |
| 4 | ABS** + 21 phr. copolymer from Example 2 and 8 phr $Sb_2O_3$ | 24.14 | Tough |
| 5 | 60% ABS** + 40% copolymer from Example 2 | 24.64 | Tough |

(*)All the materials milld well and had sufficient heat stability. All parts per hundred (phr) are based on the ABS resin as 100.
(**) Acrylonitrile-butadiene-styrene (Lustran 420 - Monsanto)
(***) Limiting Oxygen Index: The test procedue (ASTM D-2863) is described in Fenimore et al., Modern Plastics, November 1966. A higher LOI indicates better flame retardancy.
(****) The Diels-Alder diadduct of hexachlorocyclopentadiene and cyclooctadiene-1,5 (Hook Chemical Corp.)

The bromine containing copolymer of the present invention produced flame retardancy in ABS which compared favorably with the types of flame retardant ABS resins known to the prior art. The copolymer additive did not detract from the impact strength of the ABS whereas the Dechlorane produced a brittle sheet.

EXAMPLE 3

To a stirred solution of 64.8g tribromoneopentyl alcohol and 18.5g chloromethylphosphonic dichloride in 200 cc of benzene was added 34 ml of triethylamine. After the exotherm had subsided, the mixture was refluxed for 2 hours on the steam bath, was cooled, and 1 liter of water was added. The organic layer was separated and was dried over magnesium sulfate, was filtered, and was diluted with heptane. The diluted filtrate was then partly evaporated until crystals began to form, was then refrigerated overnight, and the crystalline product was then filtered off. The product, i.e., bis(tribromoneopentyl) chloromethylphosphonate, was colorless and had a melting point of 118° C. The infrared spectrum showed no OH band, but a phosphonate P=O multiplet centered at 1252 cm$^{-1}$. When applied at 15% add-on to alkali treated cellulose and heated at 150° C. for 1 hour, a wash-durable flame retardant finish is produced.

EXAMPLE 4

To a solution of 130 g (0.4 mole) tribromoneopentyl alcohol and 29.6g (0.2 mole)dimethylphosphoramidic dichloride in 200 ml. benzene was added 60 ml triethylamine. The mixture was refluxed for a period of 1½ days on a steam bath, was cooled, filtered, and the filtrate was evaporated. The residue was redissolved in chloroform, was washed with water, filtered with charcoal, diatomaceous earth and magnesium sulfate, and the filtrate then stripped at 100° C. and 0.1 mm. The product (138.4g) was a very viscous syrup, whose n.m.r. spectrum showed the P—NCH$_3$ protons at $\delta 2.75$ ppm, the P—O—CH$_2$-protons at $\delta 4.1$ ppm and the —CH$_2$Br protons at $\delta 3.6$ ppm relative to tetramethylsilane as the standard reference compound. The integrals for the three types of protons supported that the structure was $[(BrCH_2)_3CCH_2O]_2P(O)N(CH_3)_2$, i.e., bis(tribromoneopentyl)N,N-dimethylphosphoramidate. In like manner, diallylphosphoramidic dichloride is reacted with tribromoneopentyl alcohol to obtain $[(BrCH_2)_3CCH_2)]_2P(O)N(CH_2CH\!=\!CH_2)_2$, the corresponding N,N-diallyphosphoramidate, as a viscous syrup. Impregnation of cotton cloth by 20% by weight of either of the above products affords a flame retardant finish. Fixation of the N,N-dimethyl amide is achieved by warming the cloth at 160° C. for 10 minutes. The N,N-diallylamide is rendered wash durable by exposure of the impregnated cloth to 2-4 megarads of electron beam radiation.

EXAMPLE 5

A mixture of 648g (2 moles) of tribromoneopentyl alcohol and 153g (1 mole) of phosphorus oxychloride in 1000 ml of perchloroethylene is refluxed for about 3 hours until hydrogen chloride evolution dwindles to a negligible rate. The solution was cooked and filtered to remove a small by-product amount of tris(tribromoneopentyl) phosphate. The filtrate was then partially evaporated and cooled further to induce crystallization of the major product, bis(tribromoneopentyl) phosphorochloridate, as a colorless crystalline solid, m.p. 98°-99°. Analysis: Calcd. for $C_{10}H_{16}Br_6ClO_3P$: %Cl 4.9; Found: %Cl 4.9.

PREPARATION OF ESTER DERIVATIVES

Method A

To the chloride plus the indicated alcohol in equimolar amounts, dissolved in benzene, along with 50 ppm of t-butylhydroquinone is added 10% over the equimolar amount of triethylamine. After the spontaneous exotherm subsides, the mixture is heated to reflux for 3 hours, then cooled, filtered free of triethylamine hydrochloride, washed with dilute hydrochloric acid, dilute sodium carbonate solution, dried over $MgSO_4$, filtered with charcoal. The filtrate is evaporated to 100° C. under aspirator vacuum to remove solvent.

Method B

The chloride and the indicated glycidyl ester are mixed in equimolar amounts, 0.3% by weight titanium chloride is added as catalyst and the mixture is warmed on a steam bath and is held until infrared bands at 3.3 and 8 microns characteristic of the epoxy group have substantially disappeared. The product is then dissolved in chloroform, washed with dilute sodium carbonate solution, dried over $MgSO_4$, filtered with charcoal, and the filtrate evaporated to 100° C. under aspirator vacuum.

EXAMPLE 6

To a solution of 36.5g (0.05 mole) of bis(tribromoneopentyl) phosphorochloridate, made as described in Example 5, in 100 cc. of tetrahydrofuran was added 20g. (0.2 mole) of diethanolamine with stirring. The mixture was stirred for 4 hours, then diluted with 100 cc. of water causing deposition of an oil. The tetrahydrofuran was removed under aspirator vacuum and the residual crude product was a solid, m.p. 121°-130° C. The product after recrystallization from methanol-water mixture was a colorless crystalline solid, m.p. 138°-139° C., and was found to have an n.m.r. spectrum consistent with bis(tribromoneopentyl) N,N-bis(2-hydroxyethyl)phosphoramidate. Analysis: Calcd. for $C_{14}H_{26}O_5PNBr_6$: %N 1.76 Found: %N 1.60. The product when applied (in methanolic solution) to cotton-polyester at 15% dry add-on, along with dimethyloldihydroxethyleneurea at 10% dry add-on and cured in the manner of Example 1 of Weil U.S. Pat. No. 3,746,572 imparts a wash-durable flame retardant finish.

In like manner to the above preparation reaction, bis(tribromoneopentyl)phosphorochloridate in various solvents is reacted with various amines as shown in the Table:

TABLE

| AMINE | SOLVENT | PRODUCT | DESCRIPTION |
|---|---|---|---|
| Aniline | Benzene | $C_6H_5NHP(O)[OCH_2C(CH_2Br)_3]_2$ | Colorless crystalline solid, mp 95.5-96.5°. Analysis: Calcd. for $C_{16}H_{22}O_3PNBr_6$: N 1.76. Found: N 1.60. |
| Ammonia | Benzene | $NH_2P(O)[OCH_2C(CH_2Br)_3]_2$ | Colorless crystalline solid, mp 103-104.5° C. Anal: Calcd. for $C_{10}H_8O_3PNBr_6$: N 1.97. Found: N 1.98 |
| Methylamine | Benzene | $CH_3NHP(O)[OCH_2C(CH_2Br)_3]_2$ | Colorless crystalline solid |
| Monoethanolamine | Tetrahydrofuran | $HOCH_2CH_2NHP(O)[OCH_2C(CH_2Br)_3]_2$ | Colorless Wax |

The phosphoramidates given in the Table having an NH group are converted to the corresponding $-N(CH_2OH)-$ compound by heating at 80°-100° C. for 4 hours with an equimolar amount of formaldehyde (as paraformaldehyde) plus 3% triethylamine as catalyst.

EXAMPLE 7

A solution of bis(tribromoneopentyl)phosphorochloridate in benzene was stirred with water. Crystalline solids slowly came out, and were removed by filtration. The product was a colorless crystalline solid, m.p. 130° C. Titration with standard 0.1-N NaOH in aqueous acetone medium or KOH in methanol showed it to have an equivalent weight of 710 corresponding to

TABLE

| COREACTANT USED | METHOD | PRODUCT | DESCRIPTION |
|---|---|---|---|
| $CH_2=CHCOOCH_2CH_2OH$ | A | $CH_2=CHCOOCH_2CH_2OP(O)[OCH_2C(CH_2Br)_3]_2$ | Nearly colorless, waxy slid |
| $CH_2=C(CH_3)COOCH_2CH_2OH$ | A | $CH_2=C(CH_3)COOCH_2CH_2-OP(O)[OCH_2C(CH_2Br)_3]_2$ | Nearly colorless, waxy solid |
| $CH_2=CHOOC_2H_3(CH_3)OH)$ | A | $CH_2=CHCOOC_2H_3(CH_3)-OP(O)[OCH_2C(CH_2Br)_3]_2$ | Nearly colorless oil |
| $CH_2=(CH_3)COOC_2H_3(CH_3)(OH)$ | A | $CH_2=C(CH_3)COOC_2H_3(CH_3)-OP(O)[OCH_2C(CH_2Br)_3]_2$ | Nearly colorless oil |
| $HOCH_2CH_2OH$ | A | $HOCH_2CH_2OP(O)[OCH_2C(CH_2Br)_3]_2$ and $C_2H_4OP(O)[OCH_2C(CH_2Br)_3]_2$ | Colorless waxy solid |
| $HOCH_2CH_2OCH_2CH_2OH$ | A | $HOCH_2CH_2OCH_2CH_2OP(O)[OCH_2C(CH_2Br)_3]_2$ and $C_4H_8O_3(PO[OCH_2C(CH_2Br)_3]_2)_2$ | Colorless syrup |
| $CH_2=CHCOOCH_2CH\overset{O}{\underset{\diagdown}{\diagup}}CH_2$ | B | $CH_2=CHCOOC_3H_5CL-OP(O)[OCH_2C(CH_2Br)_3]_2$* | Colorless syrup |
| $CH_2=C(CH_3)COOCH_2CH\overset{O}{\underset{\diagdown}{\diagup}}CH_2$ | B | $CH_2=C(CH_3)COOC_3H_5Cl-OP(O)[OCH_2C(CH_4Br)_3]_2$* | Colorless syrup |

*The $C_3H_5Cl$ group is believed to be a mixture of $-CH(CH_2Cl)CH_2-$ and $-CH_2CH(CH_2Cl)-$ isomers

[(CHBr)₃CCH₂O]₂P(O)(OH), bis(tribromoneopentyl) hydrogen phosphate. The aqueous acetone sodium salt solution or the alcoholic potassium salt solution was applied to cotton polyester fabric to obtain a dry add-on of 20% of the alkali metal salt of bis(tribromoneopentyl) acid phosphate. Fixation of the finish was achieved by applying a solution of magnesium chloride, which gives in situ formation of the water-insoluble magnesium salt of bis(tribromoneopentyl) hydrogen phosphate. The resultant finish imparts flame retardant properties and is wash-durable.

One or more of the compounds formed herein can be used to flame retard a wide variety of normally flammable substrates by being incorporated either in or on said substrates as either an additive or as a reactant with said substrate in an amount which is effective to flame retard the substrate. Examples are fibrous materials, which for purposes of this invention include cotton, wool, silk, linen, rayons, cellulose acetate, acrylic, polyester, nylon, polyolefin, including polypropylene, blends such as cotton-polyester, and other organic fibers, yarns, and fabrics.

The polymers which can be flame retarded by the compounds of this invention include urea-aldehyde resins, melamine-aldehyde resins, urea-melamine-aldehyde resins, phenol-aldehyde resins, alkyd resins, the various vinyl type polymeric materials (both homopolymers and copolymers) including those comprising homo- and copolymers of acrylonitrile, styrene, vinyl acetate, the vinyl and vinylidene halides, butadiene, isoprene and so forth. The compounds can be incorporated in the above polymer materials during their formulation or can be used as a coating on the finished article. The amount of compound that must be incorporated either in or on the normally flammable substrate will vary between about 1 wt % and 40 wt % of the substrate depending upon the particular type of substrate chosen.

What is claimed:
1. Compounds of the formula

wherein R is a functional group selected from the group consisting of —CH=CH₂, —CH₂X, —OR'OC(O)CH=CH₂, —OR'OC(O)C(CH₃)=CH₂, —O(R'O)ₙH, —OH,Cl and —NR"R'" where R' is a C₁-C₄ alkylene or haloalkylene group, R" and R'" are the same or different and are selected from the group consisting of hydrogen, lower alkyl, phenyl, hydroxy lower alkyl, and allyl groups, X is selected from the group consisting of chlorine and bromine and $n$ is an integer between 1 and 20.

2. Bis(tribromoneopentyl) vinylphosphonate.
3. Bis(tribromoneopentyl) chloromethylphosphonate.
4. Bis(tribromoneopentyl) acryloxyethyl phosphate.
5. Bis(tribromoneopentyl) acryloxypropyl phosphate.
6. Bis(tribromoneopentyl) methacryloxyethyl phosphate.
7. Bis(tribromoneopentyl) methacryloxypropyl phosphate.
8. Bis(tribromoneopentyl) acryloxychloropropyl phosphate.
9. Bis(tribromoneopentyl) methacryloxychloropropyl phosphate.
10. Bis(tribromoneopentyl) acid phosphate.
11. Bis(tribromoneopentyl) phosphorochloridate.

* * * * *